*US009381141B2*

United States Patent
Clermont et al.

(10) Patent No.: US 9,381,141 B2
(45) Date of Patent: Jul. 5, 2016

(54) METHOD FOR MANUFACTURING A CLEANSING AND/OR CARE ARTICLE

(75) Inventors: Anne-Gaelle Clermont, Colmar (FR); Jocelyne Florence, Lapoutroie (FR); Bruno Bret, Wintzenheim (FR)

(73) Assignee: SCA TISSUE FRANCE, Saint-Ouen (FR)

( * ) Notice: Subject to any disclaimer, the term of this patent is extended or adjusted under 35 U.S.C. 154(b) by 889 days.

(21) Appl. No.: 12/738,381

(22) PCT Filed: Oct. 17, 2008

(86) PCT No.: PCT/FR2008/001465
§ 371 (c)(1),
(2), (4) Date: Jun. 30, 2010

(87) PCT Pub. No.: WO2009/083671
PCT Pub. Date: Jul. 9, 2009

(65) Prior Publication Data
US 2010/0297191 A1    Nov. 25, 2010

(30) Foreign Application Priority Data

Oct. 17, 2007   (FR) .................................... 07 07254

(51) Int. Cl.
| | |
|---|---|
| *A61K 8/25* | (2006.01) |
| *A61K 8/02* | (2006.01) |
| *A61Q 19/00* | (2006.01) |
| *A61K 8/26* | (2006.01) |

(Continued)

(52) U.S. Cl.
CPC ................ *A61K 8/0208* (2013.01); *A61K 8/26* (2013.01); *A61K 8/731* (2013.01); *A61Q 1/14* (2013.01); *A61Q 19/10* (2013.01); *A61K 2800/5424* (2013.01)

(58) Field of Classification Search
None
See application file for complete search history.

(56) References Cited

U.S. PATENT DOCUMENTS

| | | | |
|---|---|---|---|
| 3,317,395 | A | 5/1967 | Edwards |
| 3,623,990 | A | 11/1971 | Cambre |

(Continued)

FOREIGN PATENT DOCUMENTS

| | | | |
|---|---|---|---|
| EP | 0102200 A2 | 3/1984 | |
| EP | 1002746 | * 11/1998 | ............. B65D 83/08 |

(Continued)

OTHER PUBLICATIONS

Search Report and Written Opinion dated Jun. 26, 2008, for French Patent Application Publication No. 2922443 (Application No. 0707254).

(Continued)

*Primary Examiner* — Bethany Barham
*Assistant Examiner* — Dominic Lazaro
(74) *Attorney, Agent, or Firm* — Drinker Biddle & Reath LLP

(57) ABSTRACT

The invention relates to the use of a cleansing and/or care composition for impregnating a pile of absorbent supports.
The care and cleansing composition has a relatively high apparent viscosity while having a rheological behavior of the shear-thinning and thixotropic type and comprises at least one care and/or cleansing compound.
Thus, during an impregnation under stress, especially under pressure and with prior stirring, the composition becomes sufficiently fluid to enable it to rapidly and homogeneously diffuse into the supports arranged in a pile.

10 Claims, 3 Drawing Sheets

(51) Int. Cl.
  *A61K 8/73* (2006.01)
  *A61Q 1/14* (2006.01)
  *A61Q 19/10* (2006.01)

(56) References Cited

U.S. PATENT DOCUMENTS

| | | | |
|---|---|---|---|
| 3,636,200 | A | 1/1972 | Zentner |
| 3,998,973 | A | 12/1976 | Carlson |
| 4,067,962 | A | 1/1978 | Juneja |
| 4,482,538 | A | 11/1984 | Davies |
| 4,603,046 | A * | 7/1986 | Georgalas et al. ............... 424/59 |
| 4,778,048 | A * | 10/1988 | Kaspar et al. ................. 206/205 |
| 4,833,003 | A | 5/1989 | Win et al. |
| 5,013,473 | A * | 5/1991 | Norbury et al. ............... 424/452 |
| 5,084,427 | A | 1/1992 | Tsoucalas |
| 5,306,486 | A * | 4/1994 | McCook et al. ................ 424/59 |
| 6,277,798 | B1 | 8/2001 | Elliott et al. |
| 6,440,909 | B1 | 8/2002 | Vignot |
| 6,908,608 | B1 | 6/2005 | Huglin et al. |
| 2004/0228811 | A1 | 11/2004 | Krzysik |
| 2004/0242097 | A1 | 12/2004 | Hasenoehrl et al. |
| 2005/0175642 | A1 | 8/2005 | Asotra et al. |

FOREIGN PATENT DOCUMENTS

| | | |
|---|---|---|
| EP | 1043019 A1 | 10/2000 |
| EP | 1366737 A1 | 12/2003 |
| EP | 1374834 A1 | 1/2004 |
| GB | 2102290 A | 2/1983 |
| WO | 96/36758 A2 | 11/1996 |
| WO | 02/24849 A1 | 3/2002 |
| WO | 03/105804 A1 | 12/2003 |

OTHER PUBLICATIONS

Search Report and Written Opinion of the International Search Authority for PCT/FR2008/001465 that issued Dec. 3, 2010.

* cited by examiner

METHOD FOR MANUFACTURING A CLEANSING AND/OR CARE ARTICLE

BACKGROUND

The invention relates to the use of a cleansing and/or care composition, comprising at least one cleansing and/or compound, which is viscous, shear-thinning and thixotropic, for impregnating a pile of absorbent supports.

It also relates to a cleansing and/or care composition and also to a cleansing and/or care article.

It also relates to a method for manufacturing cleansing and/or care articles.

There are currently numerous preimpregnated supports, of the wet wipe type, on which cleansing and/or care products have been applied beforehand, which are used instead of the conventional dry, generally cotton, pads that the user impregnates at the moment of use.

Thus, the cleansing and/or care product may be a product for cleaning spectacles, glazing, tiled or parquet floors, a polishing product for furniture, a wax-based product for the upkeep and cleaning of wood, a cleaning product for kitchen countertops or else a waxing type product for cleaning and caring for leather.

One field particularly affected by the use of such impregnated supports is the field of body hygiene products comprising a skin cleansing and/or care product, in particular of the makeup remover type, or a skin cleansing and/or care product for babies.

In all these fields of use, these preimpregnated supports avoid, on the one hand, transporting and handling additional containers that contain the products to be impregnated and make it possible, on the other hand, to only deliver the amount required for the envisaged use.

The methods for obtaining these preimpregnated supports mainly differ from the conventional methods used to date for manufacturing the base support in that they provide a step of impregnating supports with a composition suitable for the final use of said supports.

In the case of a cosmetic use, especially removing makeup from the face, the impregnating products are generally aqueous or hydoralcoholic lotions, or liquid oil-in-water emulsions.

However, the current impregnation technologies, such as spraying or soaking, do not allow supports to be wetted in a sufficiently homogeneous and reliable manner when the products are too viscous.

This drawback is particularly pronounced when a pile of supports is impregnated by means of a single injection of liquid at the top of the pile.

It is especially observed that the viscous liquid can hardly diffuse into the supports positioned in the bottom part of the pile.

Moreover, for the supports placed in the upper part, the impregnation is not carried out in a homogeneous manner, the liquid only spreading over certain areas of the supports, the other areas being totally free thereof.

In order to solve the problem mentioned above, the solutions envisaged to date have consisted either in being limited to the impregnation of liquids that are not very viscous, or in impregnating the supports individually and no longer in a pile.

These solutions however prove not very satisfactory.

In the first case, the range of products that can potentially be used at this level is excessively limited.

Thus, in certain cosmetic applications, where the creamy and unctuous nature of the cosmetic composition is very important in the eyes of the users, the limitation on the impregnation of liquid that is not very viscous does not allow such products to be provided as preimpregnated wipes.

Moreover, the impregnation of fluid compositions into a pile of absorbent supports, such as cotton pads, generally causes a gradual diffusion, over time and from the top to the bottom of the composition in the pile: the composition is therefore no longer distributed homogeneously in the pile during a relatively long storage time.

In the second case, it is necessary to use a particularly complex and expensive technology to ensure a good impregnation of each of the supports, while substantially decreasing the production yields in comparison with those obtained during impregnation in pile.

DETAILED DESCRIPTION

The invention therefore aims to solve the problems raised by this prior art.

For this purpose, a first subject of the invention is the use of a cleansing and/or care composition at least one cleansing and/or care compound, said composition having an apparent viscosity, measured at 20° C. according to the ASTM D 2983 standard, of greater than 80 centipoise, preferably greater than 200 centipoise, more preferably greater than 500 centipoise and being shear-thinning and thixotropic, for impregnating a pile of absorbent supports.

More preferable, the cleansing and/or care composition used has an apparent viscosity, measured at 20° C. according to the ASTM D 2983 standard, or greater than 2500 centipoise, preferably greater than 12 500 centipoise.

Preferably, the cleansing and/or care composition used is comparable to a Bingham plastic until its value reaches a threshold value when it is subjected to a given shear rate.

Most preferably, the cleansing and/or care composition used has a viscosity η that decreases exponentially according to the equation:

$$B = -(d\eta/dt) \cdot t,$$

the coefficient B being greater than or equal to 0.4, preferably greater than or equal to 4, when it is subjected to a shear rate of 20 rpm using a Brookfield tester equipped with an SC4-31 reference spindle and until a threshold value of the viscosity is obtained.

Even more preferably, the cleansing and/or care composition used, when it is subjected to a shear rate of 20 rpm using a Brookfield tester equipped with an SC4-31 reference spindle and until a threshold value of the viscosity is obtained, has a viscosity ii that decreases exponentially according to the equation:

$$B = -(d\eta/dt) \cdot t,$$

the coefficient B being between 15 and 300, preferably between 200 and 300.

Still preferably, the cleansing and/or care composition used has a recovery rate RR less than or equal to 50%, preferably between 20% and 30%.

In a preferred embodiment of the use of the invention, the cleansing and/or care composition used comprises magnesium aluminum silicate and sodium carboxymethyl cellulose.

In this case, preferably, the cleansing and/or care composition comprises at least 0.4 wt %, preferably at least 0.7 wt %, more preferably at least 0.8 wt %, relative to the total weight of the composition, of magnesium aluminum silicate and at least 0.12 wt %, preferably at least 0.21 wt %, more preferably at least 0.24 wt %, relative to the total weight of said composition, of sodium carboxymethyl cellulose.

In one most particularly preferred embodiment of the use of the invention, the at least one cleansing and/or care compound is at least one skin cleansing and/or care compound.

A second subject of the invention is a method of manufacturing cleansing and/or care articles comprising the following steps:
a) stacking several absorbent supports on one another; and
b) applying, under stress, a cleansing and/or care composition comprising at least one cleansing and/or care compound, said composition having an apparent viscosity, measured at 20° C. according to the ASTM D 2983 standard, of greater than 80 centipoise, and preferably greater than 200 centipoise and being shear-thinning and thixotropic, to the absorbent support placed on the top of the stack.

More preferably, in the process of the invention, in step b), the care and/or cleansing composition has an apparent viscosity, measured at 20° C. according to the ASTM D 2983 standard of greater than 500 centipoise, preferably greater than 2500 centipoise, most preferably greater than 12 500 centipoise.

Preferably, in the method of the invention, in step b), the cleansing and/or care composition is comparable to a Bingham plastic until its viscosity reaches a threshold value.

More preferably, in the method of the invention, in step b), the cleansing and/or care composition, when it is subjected to a shear rate of 20 rpm using a Brookfield tester equipped with an SC4-31 reference spindle and until a threshold value of the viscosity is obtained, has a viscosity η that decreases exponentially according to the equation:

$$B = -(d\eta/dt) \cdot t,$$

the coefficient B being greater than or equal to 0.4, preferably greater than or equal to 4.

Even more preferably, in the method of the invention, in step b), the cleansing and/or care composition, when it is subjected to a shear rate of 20 rpm using a Brookfield tester equipped with an SC4-31 reference spindle and until a threshold value of the viscosity is obtained, has a viscosity η that decreases exponentially according to the equation:

$$B = -(d\eta/dt) \cdot t,$$

the coefficient B being between 15 and 300, preferably between 200 and 300.

Preferably, in the method of the invention, in step b), the care and/or cleansing composition applied has a recovery rate RR less than or equal to 50%, preferably between 20 and 30%.

In one preferred embodiment of the method of the invention, in step b), the cleansing and/or care composition comprises magnesium aluminum silicate and sodium carboxymethyl cellulose.

In this case, preferably, in step b), the care and/or cleansing composition comprises at least 0.4 wt %, relative to the total weight of the composition, of magnesium aluminum silicate and at least 0.12 wt %, relative to the total weight of the composition, of sodium carboxymethyl cellulose.

More preferably, in step b), the cleansing and/or care composition comprises at least 0.7 wt %, relative to the total weight of the composition, of magnesium aluminum silicate and at least 0.21 wt %, relative to the total weight of the composition, of sodium carboxymethyl cellulose.

Further still, in step b), the cleansing and/or care composition comprises at least 0.8 wt %, relative to the total weight of the composition, of magnesium aluminum silicate and at least 0.24 wt %, relative to the total weight of the composition, of sodium carboxymethyl cellulose.

A third subject of the invention is a cleansing and/or care composition particularly suitable for use according to the invention and for implementing the method of the invention.

This composition comprises at least one cleansing and/or care composition having a behavior comparable to that of a Bingham plastic until its viscosity reaches a threshold value, and an apparent viscosity, measured at 20° C. according to the ASTM D 2983 standard, of greater than 80 centipoise, more preferably greater than 200 centipoise, more preferably still greater than 500 centipoise.

Preferably, the cleansing and/or care composition of the invention has an apparent viscosity, measured at 20° C. according to the ASTM D 2983 standard, of greater than 2500 centipoise, more preferably greater that 12 500 centipoise.

Preferably, the cleansing and/or care composition of the invention, when it is subjected to a shear rate of 20 rpm using a Brookfield tester equipped with an SC4-31 reference spindle and until a threshold value of the viscosity is obtained, has a viscosity η that decreases exponentially according to the equation:

$$B = -(d\eta/dt) \cdot t,$$

the coefficient B being greater than or equal 0.4, preferably greater than or equal to 4.

More preferably, the cleansing and/or care composition of the invention, when it is subjected to a shear rate of 20 rpm using a Brookfield tester equipped with an AC4-31 reference spindle and until a threshold value of the viscosity is obtained, has a viscosity η that decreases exponentially according to the equation:

$$B = -(d\eta/dt) \cdot t,$$

the coefficient B being between 15 and 300, preferably between 200 and 300.

Preferably, the cleansing and/or care composition of the invention has a recovery rate RR less than or equal to 50%, preferably between 20 and 30%.

In one preferred embodiment, the cleansing and/or care composition of the invention comprises magnesium aluminum silicate and sodium carboxymethyl cellulose.

In this case, it comprises at least 0.4%, preferably at least 0.7%, more preferably at least 0.8%, by weight relative to the total weight of said composition, of magnesium aluminum silicate and at least 0.12%, more preferably at least 0.21%, more preferably still at least 0.24% by weight, relative to the total weight of said composition, of sodium carboxymethyl cellulose.

In one particularly preferred embodiment, the cleansing and/or composition of the invention comprises the at least one skin cleansing and/or care compound.

A fourth subject of the invention is a cleansing and/or care article composed of an absorbent support impregnated with a cleansing and/or care composition according to the invention and which releases an amount of the cleansing and/or care composition according to the invention greater than 20% for a pressure time of 120 seconds.

Preferably, in the article of the invention, the absorbent support is a cotton support.

The invention rests on the use of a cleansing and/or care composition, comprising at least one cleansing and/or care compound, which composition is viscous while having a rheological behavior of shear-thinning and thixotropic type.

In the invention, the expression "viscous composition" is understood to mean a composition for which the apparent viscosity, determined using a Brookfield viscometer, which measures the torque required to turn a Brookfield No. 2 spindle at a constant speed of 12 rpm in a bath of said composition at a given temperature of 20° C. and in accordance with the standard ASTM D 2983, is between 80 and 40 000 centipoise.

The cleansing and/or care compound may be a wax for the cleansing and care of wood, a product for cleaning windows, spectacles, tiled or parquet floors. Preferably, the at least one cleansing and/or care compound is a compound for cleansing and/or caring for the skin, more particularly the skin of babies.

By using a cleansing and/or care composition according to the invention, during an impregnation under stress, especially under pressure and with prior stirring, the composition becomes sufficiently fluid to enable it to rapidly and homogeneously diffuse into the supports arranged in a pile.

Furthermore, due to its thixotropy, the composition does not instantaneously recover its initial viscosity when it is again at rest.

This longer or shorter time makes it possible to further improve the diffusion of the composition through the supports and within each of the supports.

Moreover, when the composition has recovered its initial viscosity, it no longer migrates through the supports as a fluid composition could do: the diffusion phenomenon over time mentioned previously for fluid compositions therefore no longer occurs.

In the invention, the expression "viscous composition" is understood to mean a composition for which the apparent viscosity is between 80 and 40 000 centipoise, determined using a Brookfield viscometer, which measures the torque required to turn a Brookfield No. 2 spindle at a constant speed of 12 rpm in a bath of said composition at a given temperature of 20° C. and in accordance with the ASTM D 2983 standard.

Other advantages and features will appear more clearly from the description which follows of some exemplary embodiments according to the inventions.

EXAMPLE 1

A cosmetic composition was prepared containing the following ingredients:
  0.3% of magnesium aluminum silicate;
  0.09% of carboxymethyl cellulose;
  0.1% of tetrasodium EDTA;
  0.25% of chlorphenesin;
  3.0% of glycerin;
  0.9% of a mixture of butylparaben, propylparaben, isobutylparaben, phenoxyethanol, methylparaben and ethylparaben;
  3.0% of a mixture of ceteareth-20, ceteareth-12, cetearyl alcohol, cetyl palmitate and glyceryl stearate;
  1.0% of ceteareth-20;
  6.0% of a mineral oil;
  2.0% of isohexadecane;
  1.0% of caprylic/capric triglyceride;
  1.0% of polydimethylsiloxane;
  0.15% of fragrance;
  1.0% of a mixture of glycerin, butylene glycol, water and plant extracts; and
  80.2% of water.

The rheological characteristics of this composition were determined by first measuring its apparent viscosity in centipoise, determined using a Brookfield viscometer which measured the torque required to turn a Brookfield No. 2 spindle at a constant speed of 12 rpm in a bath of said composition at a given temperature of 20° C. and in accordance with the standard ASTM D 2983.

The viscosity measured was 85 cP.

The rheological behavior of this composition was then characterized, especially its variations in viscosity as a function of time, when it was subjected to a constant shear stress.

For that purpose a Brookfield tester, sold under the reference Rheocalc data 1 LV, equipped with an SC4-31 reference spindle rotating at 20 rpm was used.

Figure 1:
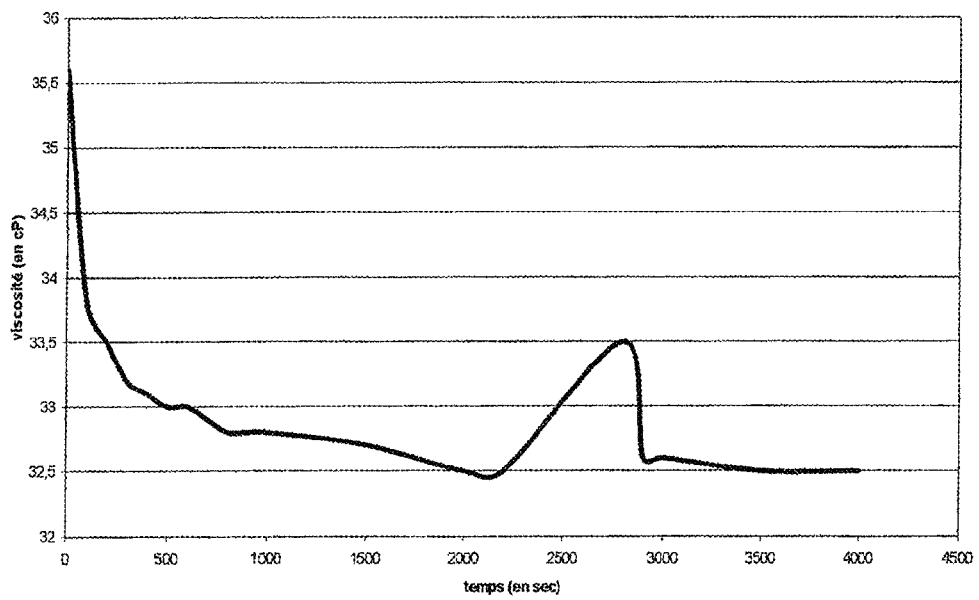
FIG. 1 is a graph illustrating viscosity values versus time for Example 1.

The viscosity values taken in this level have been collated in Table 1 and the corresponding graph has been represented in FIG. 1.

It can firstly be seen that the viscosity decreases as a function of time according to a substantially exponential law before reaching a threshold value.

The viscous composition therefore has a shear-thinning behavior.

Therefore, until its viscosity reaches the threshold value, it is comparable to a Bingham plastic for which the viscosity $\eta$ of the composition decreases exponentially according to the equation:

$$B = -(d\eta/dt) \cdot t,$$

B being the thixotropic destruction temporal coefficient.

It was determined, by calculation and by extrapolation, that B was equal, in this case to 0.40.

In order to characterize the thixotropy of this composition, the shear stress was furthermore stopped, preferably when the viscosity of the composition had already reached its threshold value $\eta_1$, before restarting the same stress after a waiting time of 10 minutes.

It is observed in Table 1 and in FIG. 1 that the viscosity $\eta_2$ of the composition measured just before restarting the shear stress is substantially lower than the viscosity $\eta_0$ of the composition at the start.

This is because the viscosity recovery of the thixotropic composition is not immediate after the shear stress has been stopped.

To characterize this phenomenon, the recovery rate RR of this composition was evaluated after a rest period of 10 minutes, which corresponds to:

$$RR = (\eta_2 - \eta_1)/(\eta_0 - \eta_1) \times 100$$

which gives, in this case, a recovery rate RR of around 30%.

The lower the recovery rate RR, the more thixotropic the composition.

Next, the improved impregnating ability of this composition was evaluated.

For that, a stack of five 120 g/m² makeup-removing pads made of 100% cotton fibers, manufactured by the Applicant from laps described in European Patent No. 0 681 621, were impregnated by depositing an amount of said composition on the pad positioned on the top of the pile. The amount of composition deposited was calculated to correspond to a final impregnation of 1 g per gram of cotton.

Two series of measurements were carried out.

In the first series, the composition was left to diffuse through the pile of cotton pads without applying any stress.

In the second series, a continuous stress was applied to the pile just after the deposition of the composition by means of a 5.2 kg load.

In each of the series of measurements, a waiting period of 5 minutes was observed after the deposition and each of the cotton pads was weighed.

Knowing the weight of the pad at the start, it is possible to calculate the weight of composition absorbed inside the cotton, then the percentage of the total composition which that represents.

The results are collated in Table 2.

It is observed that the composition diffuses better inside the pile when it is subjected to a stress.

This obviously results from the shear-thinning behavior of the composition, which induces a drop in viscosity in the case of stress and, therefore, improves the diffusion in the pile.

Also evaluated was the ability of a cotton pad impregnated with said composition to release this composition, under stress, onto a transfer surface in contact with said cotton pad.

For that, 120 g/m$^2$ makeup-removing pads made of 100% cotton fibers, manufactured by the Applicant from laps described in European Patent No. 0 681 621 were impregnated with the preceding composition and according to a content of around 4 grams of composition per gram of cotton. Then, the amount of composition released by application of a load on the pad was measured.

The procedure was the following:
1) the pad impregnated with the composition was weighed using a balance to within 0.01 g: thus the weight M1 was determined;
2) blotting paper (Whatman 201 (ref. 5201-930)) was prepared, cut (diameter of 112 mm or square with sides of 145 mm) with a punch or using scissors;
3) the impregnated pad was placed on 10 layers of blotting paper and it was covered with 10 more layers of blotting paper;
4) a load of 3.5 kg was placed on the sandwich of material obtained for a set time t. Since the pad had a surface area of around 25.5 cm$^2$ (disc of diameter 57 mm), the average pressure applied to it by the load was equal to around 138 g/cm$^2$. This value corresponded to a relatively low pressure, normally below the pressure generally exerted by the fingers on the face when operating on the face;
5) the load was removed and the pad was weighed; the difference between the weight M1 of the pad before compression and the weight M2 of the pad after compression determined the amount of lotion extracted;
6) the pad was rinsed with hot water to remove the rest of the lotion, then it was left to dry in an oven for 2 hours at 100° C.;
7) the weight M3 of the dry pad was measured; and
8) thus the impregnation rate of the pad at the start of the test was determined:

$$IR=(M1-M3)/M3,$$

and also the amount of composition released was determined by the format (release rate):

$$LR=(M1-M2)/(M1-M3).$$

The results are collated in Table 3.

The measurements were carried out for respective compression times of 10, 30, 60 and 120 seconds.

It is observed that, even for a compression time of 10 seconds, the release rate is greater than 20%, which corresponds to an average release rate measured on commercial carded cotton pads having a basis weight equal to 100 g/m$^2$ and subjected to a pressure of 300 g/cm$^2$ for 60 seconds.

Moreover, this rate of lotion released by the pad increased rapidly with the compression time due to the shear-thinning behavior of the composition.

In particular, it is observed that the release rate for a compression time of 120 seconds is 40.6%

This gives, at the end, the impregnated cotton pad, under the normal conditions of use, very good cosmetic product release characteristics.

Furthermore, these characteristics are obtained without the user needing to exert a high pressure on their face, which forms an additional advantage of the invention.

EXAMPLE 2

A cosmetic composition was prepared containing the following ingredients:
   0.4% of magnesium aluminum silicate;
   0.12% of carboxymethyl cellulose;
   0.1% of tetrasodium EDTA;
   0.2% of chlorphenesin;
   3.0% of glycerin;
   0.8% of a mixture of butylparaben, propylparaben, isobutylparaben, phenoxyethanol, methylparaben and ethylparaben;
   3.0% of a mixture of ceteareth-20, ceteareth-12, cetearyl alcohol, cetyl palmitate and glyceryl stearate;
   1.0% of ceteareth-20;
   6.0% of a mineral oil;
   2.0% of isohexadecane;
   1.0% of caprylic/capric triglyceride;
   1.0% of polydimethylsiloxane;
   0.15% of fragrance;
   1.0% of a mixture of glycerin, butylene glycol, water and plant extracts; and
   80.23% of water.

This composition was then subjected to the same measurements as described previously in Example 1.

Thus, an apparent viscosity was determined for the composition of 525 cP.

Figure 2:
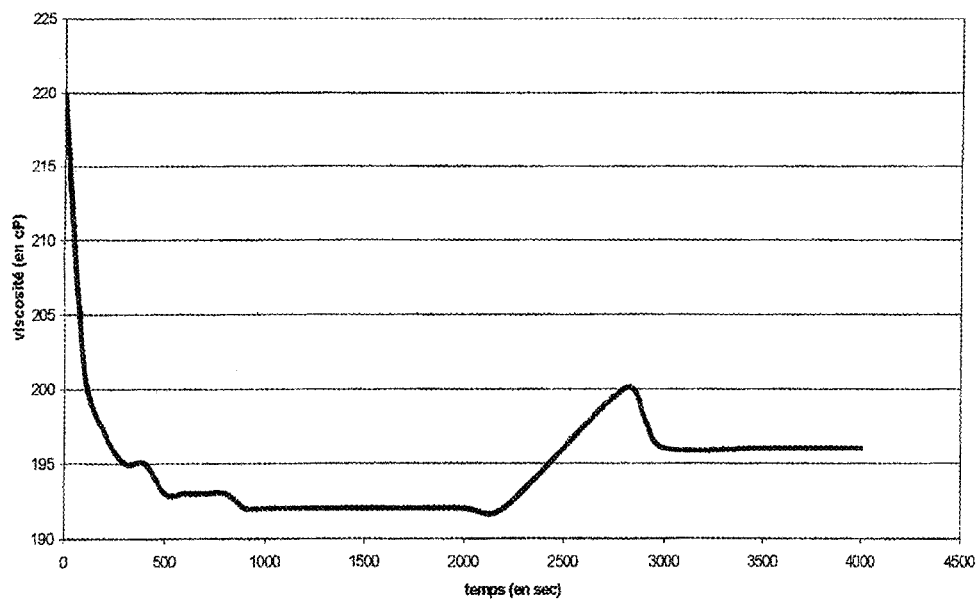
FIG. 2 is a graph illustrating viscosity values versus time for Example 2.

By measuring the variations in viscosity as a function of time, when the composition was subjected to a constant shear stress, values which are collated in Table 1 and represented in FIG. 2, it was observed that the composition had a shear-thinning behavior and was comparable to a Bingham plastic, until its viscosity reached a threshold value.

In this case, it was determined, by the calculation, that the composition had a thixotropic destruction temporal coefficient B equal to 4.34 and recovery rate RR equal to 28%.

Next, the improved impregnating ability of this composition was evaluated.

The results are collated in Table 2.

It was observed, as in Example 1, that the composition diffuses better within the pile when it is subjected to a stress.

Also evaluated was the ability of a cotton pad impregnated with said composition to release this composition, under stress, onto a transfer surface in contact with said cotton pad.

The results are collated in Table 3.

It was observed that, even when the release rate for a compression time of 10 seconds was below 20%, which corresponded to the average release rate measured on commercial carded cotton pads having a basis weight equal to 100 g/m$^2$ and subjected to a pressure of 300 g/cm$^2$ for 60 seconds, the amount of lotion released by the pad increased rapidly with the compression time due to the shear-thinning behavior of the composition.

In particular, it was observed that the release rate for a compression time of 120 seconds was at least 30%.

EXAMPLE 3

A cosmetic composition was prepared containing the following ingredients:
- 0.7% of magnesium aluminum silicate;
- 0.21% of carboxymethyl cellulose;
- 0.1% of tetrasodium EDTA;
- 0.2% of chlorphenesin;
- 3.0% of glycerin;
- 0.8% of a mixture of butylparaben, propylparaben, isobutylparaben, phenoxyethanol, methylparaben and ethylparaben;
- 3.0% of a mixture of ceteareth-20, ceteareth-12, cetearyl alcohol, cetyl palmitate and glyceryl stearate;
- 1.0% of ceteareth-20;
- 6.0% of a mineral oil;
- 2.0% of isohexadecane;
- 1.0% of caprylic/capric triglyceride;
- 1.0% of polydimethylsiloxane;
- 0.15% of fragrance;
- 1.0% of a mixture of glycerin, butylene glycol, water and plant extracts; and
- 79.84% of water.

This composition was then subjected to the same measurements as described previously in Example 1.

Thus, an apparent viscosity was determined for the composition of 2645 cP.

Figure 3:
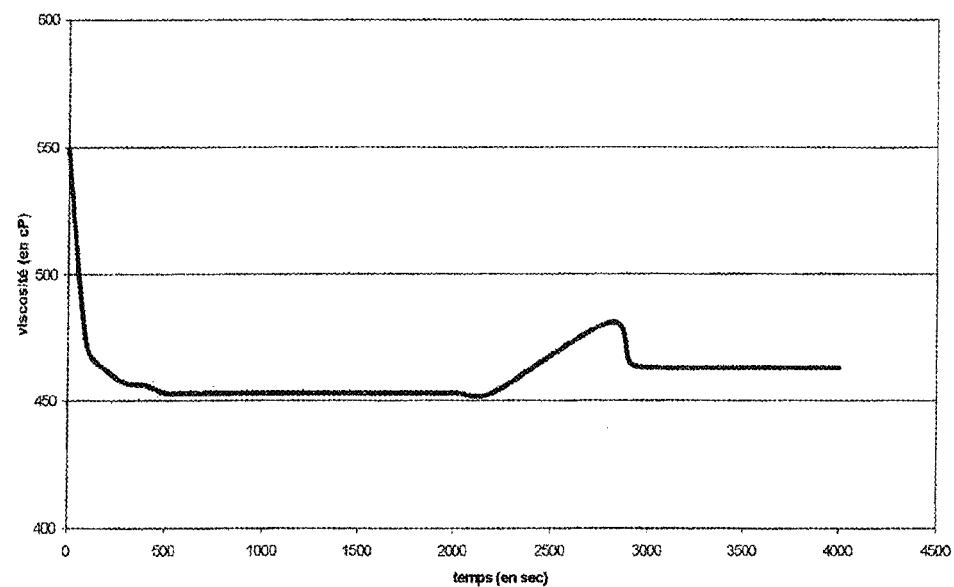
FIG. 3 is a graph illustrating viscosity values versus time for Example 3.

By measuring the variations in viscosity as a function of time, when the composition was subjected to a constant shear stress, values which are collated in Table 1 and represented in FIG. 3, it was observed that the composition had a shear-thinning behavior and was comparable to a Bingham plastic, until its viscosity reached a threshold value.

In this case, it was determined, by the calculation, that the composition had a thixotropic destruction temporal coefficient B equal to 14.96 and a recovery rate RR equal to 29%.

Next, the improved impregnating ability of this composition was evaluated.

The results are collated in Table 2.

It was observed, as in Example 1, that the composition diffuses better within the pile when it is subjected to a stress.

Also evaluated was the ability of a cotton pad impregnated with said composition to release this composition, under stress, onto a transfer surface in contact with said cotton pad.

The results are collated in Table 3.

It was observed that, even when the release rate for a compression time of 10 seconds was below 20%, which corresponded to the average release rate measured on commercial carded cotton pads having a basis weight equal to 100 g/m$^2$ and subjected to a pressure of 300 g/cm$^2$ for 60 seconds, the amount of lotion released by the pad increased rapidly with the compression time due to the shear-thinning behavior of the composition.

In particular, it was observed that the release rate for a compression time of 120 seconds was at least 30%.

EXAMPLE 4

A cosmetic composition was prepared containing the following ingredients:
- 0.8% of magnesium aluminium silicate;
- 0.24% of carboxymethyl cellulose;
- 0.1% of tetrasodium EDTA;
- 0.2% of chlorphenesin;
- 3.0% of glycerin;
- 0.8% of a mixture of butylparaben, propylparaben, isobutylparaben, phenoxyethanol, methylparaben and ethylparaben;
- 3.0% of a mixture of ceteareth-20, ceteareth-12, cetearyl alcohol, cetyl palmitate and glyceryl stearate;
- 1.0% of ceteareth-20;
- 6.0% of a mineral oil;
- 2.0% of isohexadecane;
- 1.0% of caprylic/capric triglyceride;
- 1.0% of polydimethylsiloxane;
- 0.15% of fragrance;
- 1.0% of a mixture of glycerin, butylene glycol, water and plant extracts; and
- 79.71% of water.

This composition was then subjected to the same measurements as described previously in Example 1.

Thus, an apparent viscosity was determined for the composition of 12500 cP.

Figure 4:
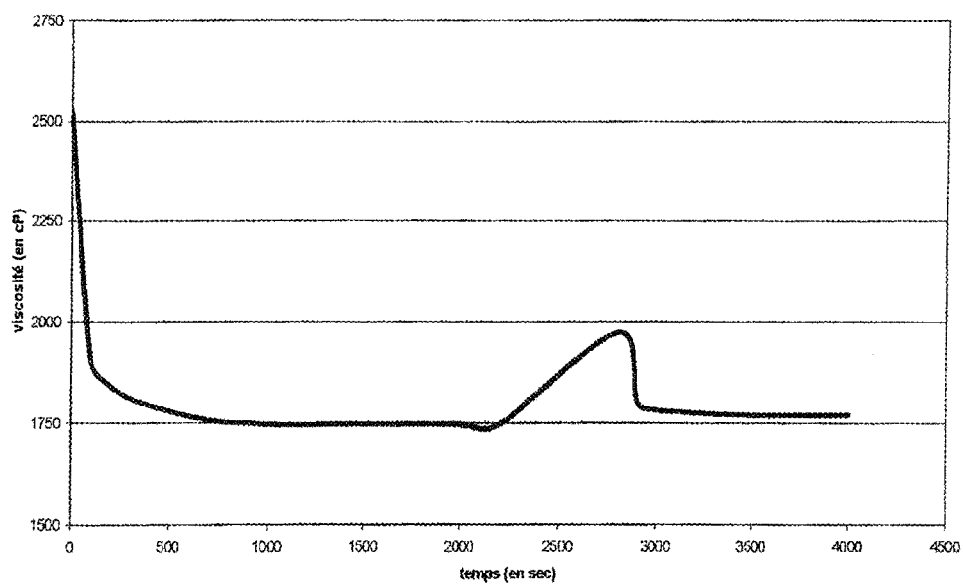
FIG. 4 is a graph illustrating viscosity values versus time for Example 4.

By measuring the variations in viscosity as a function of time, when the composition was subjected to a constant shear stress, values which are collated in Table 1 and represented in FIG. 4, it was observed that the composition had a shear-thinning behavior and was comparable to a Bingham plastic, until its viscosity reached a threshold value.

In this case, it was determined, by the calculation, that the composition had a thixotropic destruction temporal coefficient B equal to 108.57 and a recovery rate RR equal to 29%.

Next, the improved impregnating ability of this composition was evaluated.

The results are collated in Table 2.

It was observed, as in Example 1, that the composition diffuses better with the pile when it is subjected to a stress.

Also evaluated was the ability of a cotton pad impregnated with said composition to release this composition, under stress, onto a transfer surface in contact with said cotton pad.

The results are collated in Table 3.

It was observed that, even when the release rate for a compression time of 10 seconds was below 20%, which corresponded to the average release rate measured on commercial carded cotton pads having a basis weight equal to 100 g/m$^2$ and subjected to a pressure of 300 g/cm$^2$ for 60 seconds, the amount of lotion released by the pad increased rapidly with the compression time due to the shear-thinning behavior of the composition.

In particular, it was observed that the release rate for a compression time of 120 seconds was at least 25%.

EXAMPLE 5

A cosmetic composition was prepared containing the following ingredients:
- 1.6% of magnesium aluminium silicate;
- 0.48% of carboxymethyl cellulose;
- 0.1% of tetrasodium EDTA;
- 0.2% of chlorphenesin;
- 3.0% of glycerin;

0.8% of a mixture of butylparaben, propylparaben, isobutylparaben, phenoxyethanol, methylparaben and ethylparaben;

3.0% of a mixture of ceteareth-20, ceteareth-12, cetearyl alcohol, cetyl palmitate and glyceryl stearate;

1.0% of ceteareth-20;

6.0% of a mineral oil;

2.0% of isohexadecane;

1.0% of caprylic/capric triglyceride;

1.0% of polydimethylsiloxane;

0.15% of fragrance;

1.0% of a mixture of glycerin, butylene glycol, water and plant extracts; and 78.67% of water.

This composition was then subjected to the same measurements as described previously in Example 1.

Thus, an apparent viscosity was determined for the composition of 24 000 cP.

Figure 5:
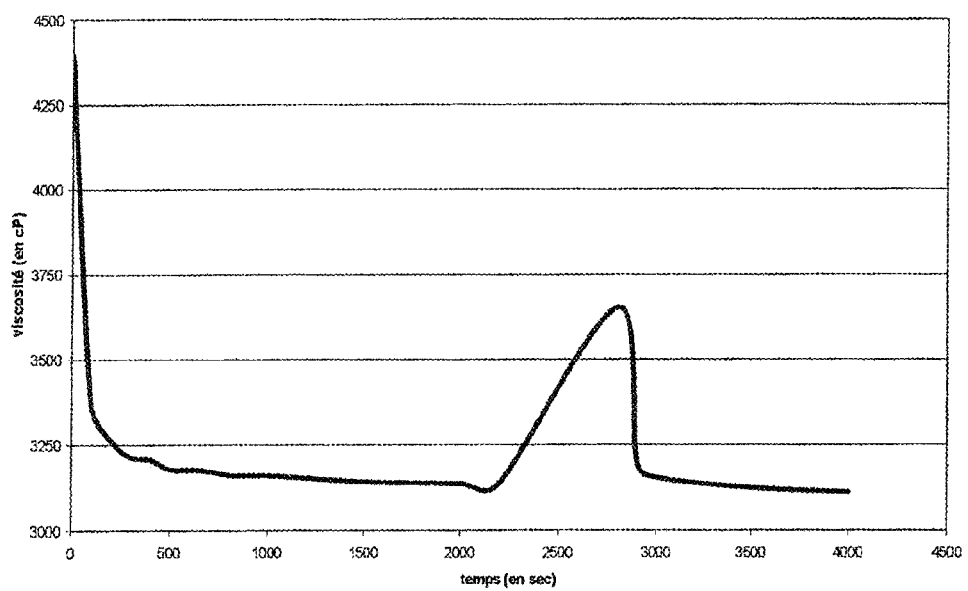
FIG. 5 is a graph illustrating viscosity values versus time for Example 5.

By measuring the variations in viscosity as a function of time, when the composition was subjected to a constant shear stress, values which are collated in Table 1 and represented in FIG. 5, it was observed that the composition had a shear-thinning behavior and was comparable to a Bingham plastic, at least during the first seconds of measurements.

Thus, it was determined, by the calculation, that the composition had a thixotropic destruction temporal coefficient B equal to 209.18 and a recovery rate RR equal to 41%.

Next, the improved impregnating ability of this composition was evaluated.

The results are collated in Table 2.

It was observed, as in Example 1, that the composition diffuses better within the pile when it is subjected to a stress.

Also evaluated was the ability of a cotton pad impregnated with said composition to release this composition, under stress, onto a transfer surface in contact with said cotton pad.

The results are collated in Table 3.

In particular, it was observed that the release rate for a compression time of 120 seconds was at least 21%.

TABLE 1

| Time (s) | Example 1 Viscosity (cP) | Example 2 Viscosity (cP) | Example 3 Viscosity (cP) | Example 4 Viscosity (cP) | Example 5 Viscosity (cP) |
| --- | --- | --- | --- | --- | --- |
| 0 | 35.6 | 220 | 549 | 2525 | 4397 |
| 100 | 33.8 | 201 | 472 | 1908 | 3371 |
| 200 | 33.5 | 197 | 462 | 1842 | 3263 |
| 300 | 33.2 | 195 | 457 | 1812 | 3215 |
| 400 | 33.1 | 195 | 456 | 1794 | 3208 |
| 500 | 33.0 | 193 | 453 | 1780 | 3179 |
| 600 | 33.0 | 193 | 453 | 1768 | 3178 |
| 700 | 32.9 | 193 | 453 | 1758 | 3173 |
| 800 | 32.8 | 193 | 453 | 1752 | 3162 |
| 900 | 32.8 | 192 | 453 | 1750 | 3161 |
| 1000 | 32.8 | 192 | 453 | 1746 | 3161 |
| 1500 | 32.7 | 192 | 453 | 1746 | 3143 |
| 2000 | 32.6 | 192 | 453 | 1746 | 3137 |
| 2200 (stirring stopped) | 32.6 | 192 | 453 | 1746 | 3137 |
| 2800 (stirring restarted) | 33.5 | 200 | 481 | 1974 | 3653 |
| 2900 | 32.6 | 198 | 465 | 1800 | 3197 |
| 3000 | 32.6 | 196 | 463 | 1782 | 3155 |
| 3500 | 32.5 | 196 | 463 | 1770 | 3125 |
| 4000 | 32.5 | 196 | 463 | 1770 | 3113 |
| $\eta 0$ | 35.6 | 220 | 549 | 2525 | 4397 |
| $\eta 1$ | 32.6 | 192 | 453 | 1746 | 3137 |
| $\eta 2$ | 33.5 | 200 | 481 | 1974 | 3653 |

TABLE 2

| | Example 1 % composition | | Example 2 % composition | | Example 3 % composition | | Example 4 % composition | | Example 5 % composition | |
| --- | --- | --- | --- | --- | --- | --- | --- | --- | --- | --- |
| Pad No. | $1^{st}$ series | $2^{nd}$ series | $1^{st}$ series | $2^{nd}$ series | $1^{st}$ series | $2^{nd}$ series | $1^{st}$ series | $2^{nd}$ series | $1^{st}$ series | $2^{nd}$ series |
| 1 | 34 | 29 | 40 | 33 | 41 | 33 | 76 | 38 | 97 | 48 |
| 2 | 29 | 27 | 30 | 26 | 33 | 29 | 24 | 33 | 3 | 36 |
| 3 | 20 | 21 | 21 | 21 | 21 | 22 | 0 | 21 | 0 | 15 |
| 4 | 12 | 15 | 8 | 13 | 5 | 12 | 0 | 7 | 0 | 1 |
| 5 | 5 | 8 | 1 | 7 | 0 | 4 | 0 | 1 | 0 | 0 |

TABLE 3

| | Example 1 | Example 2 | Example 3 | Example 4 | Example 5 |
| --- | --- | --- | --- | --- | --- |
| M1 (g) | 2.17 | 2.08 | 2.13 | 2.13 | 2.19 |
| M3 (g) | 0.44 | 0.42 | 0.43 | 0.43 | 0.44 |
| IR (g/g) | 4.0 | 4.0 | 3.9 | 4.0 | 3.9 |
| M2 (10 sec) (g) | 1.77 | 1.76 | 1.87 | 1.93 | 2.01 |
| M2 (30 sec) (g) | 1.63 | 1.64 | 1.75 | 1.83 | 1.93 |
| M2 (60 sec) (g) | 1.54 | 1.55 | 1.67 | 1.76 | 1.87 |
| M2 (120 sec) (g) | 1.47 | 1.53 | 1.61 | 1.69 | 1.81 |
| LR (10 sec) (%) | 22.9 | 19.1 | 15.5 | 11.8 | 10.0 |
| LR (30 sec) (%) | 31.2 | 26.8 | 22.3 | 17.6 | 14.6 |
| LR (60 sec) (%) | 36.3 | 31.7 | 26.9 | 21.5 | 18.5 |
| LR (120 sec) (%) | 40.6 | 36.0 | 30.7 | 25.7 | 21.6 |

The invention claimed is:

1. A method of manufacturing skin care articles comprising:

stacking several absorbent pads on one another;

applying the whole desired volume of a skin care composition, comprising at least one skin care compound, said composition having an apparent viscosity, measured at 20° C. according to the ASTM D 2983 standard, of greater than 80 centipoise and being shear-thinning and thixotropic, to the absorbent pad placed on the top of the stack in the absence of an additional stress to the stack; and after the application of the skin care composition to the absorbent pad placed on the stack of several absorbent pads, subjecting the stack of several absorbent pads to a stress by the application of a load, thereby impregnating all the absorbent pads of the stack with one application of the skin care composition to the absorbent pad placed on the top of the stack.

2. The method of claim 1, wherein the skin care composition has an apparent viscosity, measured according to the ASTM D 2983 standard, of greater than 500 centipoise.

3. The method of claim 1, wherein the skin care composition is comparable to a Bingham plastic until its viscosity reaches a threshold value.

4. The method of claim 1, wherein the skin care composition, when it is subjected to a shear rate of 20 rpm using a Brookfield tester equipped with an SC4-31 reference spindle and until a threshold value of the viscosity is obtained, has a viscosity η that decreases exponentially according to the equation:

$$B=-(d\eta/dt)*t,$$

the coefficient B being greater than or equal to 0.4, wherein B is a thixotropic destruction temporal coefficient and t is time.

5. The method as claimed in claim 1, wherein the skin care composition, when it is subjected to a shear rate of 20 rpm using a Brookfield tester equipped with an SC4-31 reference spindle and until a threshold value of the viscosity is obtained, has a viscosity η that decreases exponentially according to the equation:

$$B=-(d\eta/dt)*t,$$

the coefficient B being between 15 and 300, wherein B is a thixotropic destruction temporal coefficient and t is time.

6. The method of claim 1, wherein the skin care composition has a recovery rate less than or equal to 50%.

7. The method of claim 1, wherein the skin care composition comprises magnesium aluminum silicate and sodium carboxymethyl cellulose.

8. The method of claim 7, wherein the skin care composition comprises at least 0.4 wt %, relative to the total weight of the composition, of magnesium aluminum silicate and at least 0.12 wt %, relative to the total weight of the composition, of sodium carboxymethyl cellulose.

9. The method as claimed in claim 7, wherein the skin care composition comprises at least 0.7 wt %, relative to the total weight of the composition, of magnesium aluminum silicate and at least 0.21 wt %, relative to the total weight of the composition, of sodium carboxymethyl cellulose.

10. The method of claim 7, wherein the skin care composition comprises at least 0.8 wt %, relative to the total weight of the composition, of magnesium aluminum silicate and at least 0.24 wt %, relative to the total weight of the composition, of sodium carboxymethyl cellulose.

* * * * *